US00PP15943P2

(12) United States Plant Patent
van der Maat

(10) Patent No.: US PP15,943 P2
(45) Date of Patent: Sep. 6, 2005

(54) JAPANESE MAPLE PLANT NAMED 'TAYLOR'

(50) Latin Name: *Acer palmatum*
Varietal Denomination: Taylor

(75) Inventor: Diana van der Maat, Boskoop (NL)

(73) Assignee: Witteman & Company, Hillegom (NL)

( * ) Notice: Subject to any disclaimer, the term of this patent is extended or adjusted under 35 U.S.C. 154(b) by 50 days.

(21) Appl. No.: 10/878,425

(22) Filed: Jun. 28, 2004

(51) Int. Cl.[7] ..... A01H 5/00
(52) U.S. Cl. ..... Plt./224

(58) Field of Search ..... Plt./224

(56) References Cited

PUBLICATIONS

UPOV hit on 'Taylor', UPOV–Rom Feb. 15, 2003.*

* cited by examiner

*Primary Examiner*—Anne Marie Grunberg
(74) *Attorney, Agent, or Firm*—C. A. Whealy

(57) ABSTRACT

A new and distinct cultivar of Japanese Maple plant named 'Taylor', characterized by its upright plant habit; brownish red-colored stems; and green and pink bi-colored leaves.

1 Drawing Sheet

Botanical classification/cultivar designation: *Acer palmatum* cultivar Taylor.

BACKGROUND OF THE INVENTION

The present Invention relates to a new and distinct cultivar of Japanese Maple plant, botanically known as *Acer palmatum*, and hereinafter referred to by the cultivar name Taylor.

The Japanese Maple originated from a cross-pollination during the spring of 1996 in Boskoop, The Netherlands of two unknown selections of *Acer palmatum*, not patented. The new Japanese Maple was discovered and selected by the Inventor as a single plant within the progeny of the stated cross-pollination in a controlled environment in Boskoop, The Netherlands during the summer of 1998.

Asexual reproduction of the new cultivar by grafting at Boskoop, The Netherlands since 1998, has shown that the unique features of this new Japanese Maple are stable and reproduced true to type in successive generations.

SUMMARY OF THE INVENTION

Plants of the cultivar Taylor have not been observed under all possible environmental conditions. The phenotype may vary somewhat with variations in environment such as temperature and light level without, however, any variance in genotype.

The following traits have been repeatedly observed and are determined to be the unique characteristics of 'Taylor'. These characteristics in combination distinguish 'Taylor' as a new and distinct cultivar of Japanese Maple:

1. Upright plant habit.
2. Brownish red-colored stems.
3. Green and pink bi-colored leaves.

Plants of the new Japanese Maple can be compared to the Japanese Maple cultivar Beni Shichi Henge. Plants of the new Japanese Maple and the cultivar Beni Shichi Henge differ in leaf and stem coloration as plants of the cultivar Beni Shichi Henge do not have orange pink-colored developing leaves and have green-colored stems.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Japanese Maple.

The photograph at the top of the sheet comprises a side perspective view of a typical plant of 'Taylor'.

The photograph at the center of the sheet is a close-up view of typical developing leaves of 'Taylor'.

The photograph at the bottom of the sheet is a close-up view of typical fully expanded leaves of 'Taylor'.

DETAILED BOTANICAL DESCRIPTION

The aforementioned photographs, following observations and measurements describe plants grown in Boskoop, The Netherlands, in an outdoor nursery and under commercial production practices in September. Plants were grown in 9-cm containers and were about two months old when the photographs and description were taken. During the production of the plants, day temperatures ranged from 14 to 32° C. and night temperatures ranged from about 10 to 20° C. In the following description, color references are made to The Royal Horticultural Society Colour Chart, 2001 Edition, except where general terms of ordinary dictionary significance are used.

Botanical classification: *Acer palmatum* cultivar Taylor.
Parentage:

*Female, or seed parent.*—Unknown selection of *Acer palmatum*, not patented.

*Male, or pollen parent.*—Unknown selection of *Acer palmatum*, not patented.

Propagation:

*Type.*—By grafting.

*Time to initiate new growth.*—About three weeks after grafting, new growth is observed.

Plant description:

*Plant form/habit.*—Upright deciduous tree; moderately vigorous growth habit.

*Plant height.*—About 25 cm.

*Plant width* (*spread*).—About 13 cm.

*Lateral branch description.*—Number per plant: About six. Length: About 4 cm. Diameter: About 2 mm. Internode length: About 4.8 cm. Texture: Smooth, glabrous. Strength: Strong. Color: 177A to 178A.

*Foliage description.*—Arrangement: Opposite, simple. Leaflet length: About 5.5 cm. Leaflet width: About 5.2 cm. Shape: Palmate, five-parted. Apex: Acute. Base: Reniform to hastate. Margin: Irregularly biserrate. Texture, upper and lower surfaces: Smooth, glabrous. Venation pattern: Palmate. Color: Developing leaves, upper surface: Center, 143B to 143C; towards the margins, 48A to 48B to 51C. Venation, 150D to 157A. Developing leaves, lower surface: Center, 143C; towards the margins, 39B. Venation, 144D. Fully expanded leaves, upper surface: Center, 137A; towards the margins, 38A to 38B to 39C; towards the leaf base, 157A to 157B. Venation, 138B. Fully expanded leaves, lower surface: Center, 137A to 137B; towards the margins, 38B to 39C; towards the leaf base, 157A to 157B. Venation, 143A. Petiole: Length: About 2.1 cm. Diameter: About 1 mm. Texture, upper and lower surfaces: Smooth, glabrous. Color, upper surface: 175B to 175C; towards the leaf, 144B. Color, upper surface: 144A, slightly overlain with N170B.

Flower description: Flower development has not been observed on plants of the new Japanese Maple.

Disease/pest resistance: Plants of the new Japanese Maple have not been noted to be resistant to pathogens and pests common to Japanese Maple.

Temperature tolerance: Plants of the new Japanese Maple have been observed to tolerate temperatures from −10 to 35° C.

It is claimed:

1. A new and distinct cultivar of Japanese Maple plant named 'Taylor', as illustrated and described.

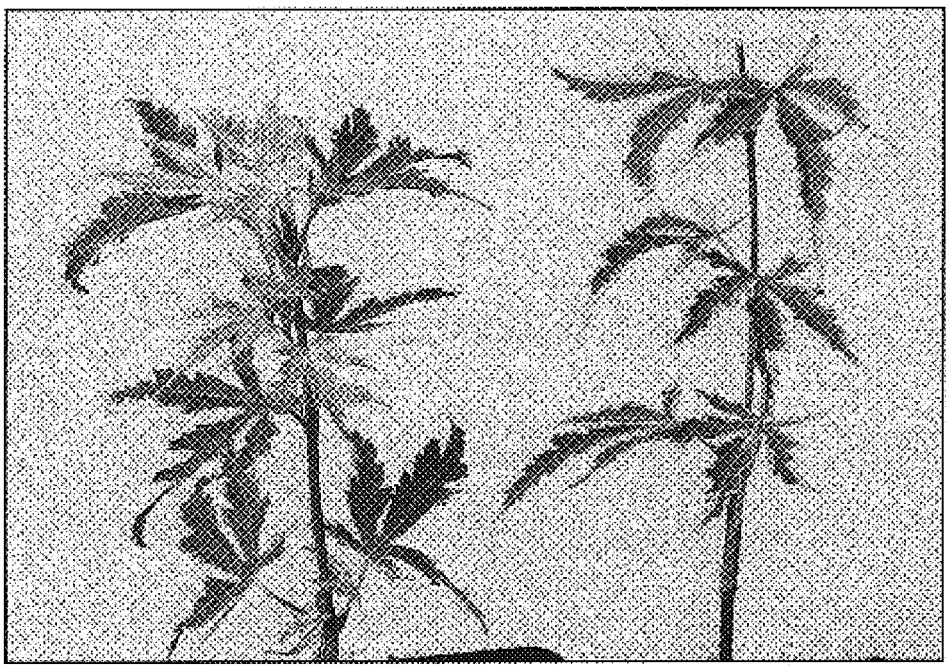
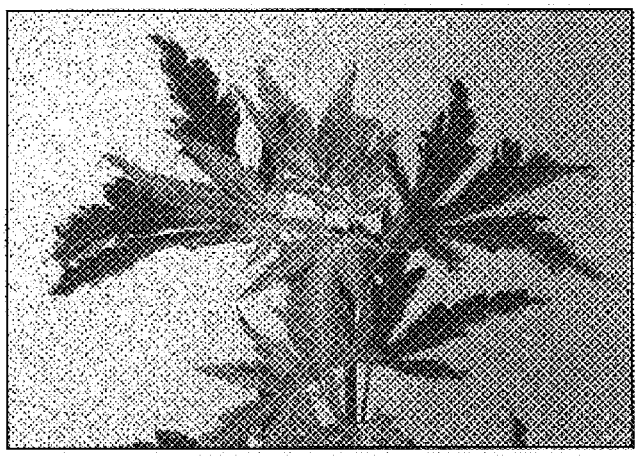
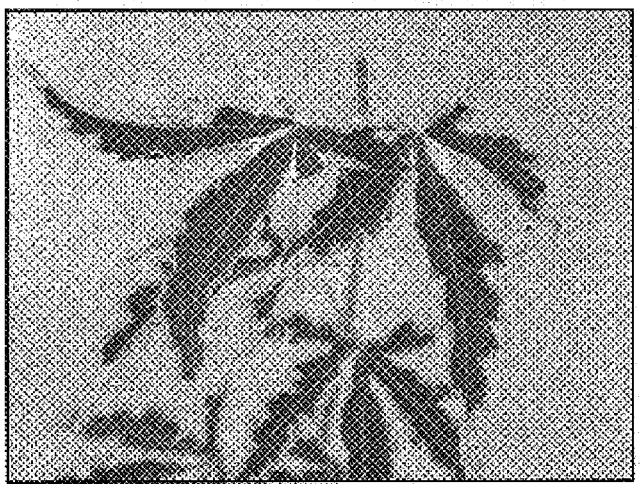

* * * * *